United States Patent [19]

Arndt et al.

[11] 4,164,414
[45] Aug. 14, 1979

[54] N-METHYLCARBANILIC-[3-(ETHOXYCARBONYLAMINO)-PHENYL]-ESTER AS A COTTON HERBICIDE

[75] Inventors: Friedrich Arndt; Gerhard Boroschewski, both of Berlin, Fed. Rep. of Germany

[73] Assignee: Schering Aktiengesellschaft, Berlin and Bergkamen, Fed. Rep. of Germany

[21] Appl. No.: 770,492

[22] Filed: Feb. 22, 1977

[30] Foreign Application Priority Data

Feb. 26, 1976 [DE] Fed. Rep. of Germany ....... 2608473

[51] Int. Cl.² .......................... A01N 9/20; C07C 79/46
[52] U.S. Cl. ........................................ 71/111; 560/24; 560/25
[58] Field of Search ...................... 71/111; 260/471 C; 560/24, 25

[56] References Cited

PUBLICATIONS

Thompson, Agricultural Chemicals–Book II Herbicides–p. 83.

*Primary Examiner*—Catherine L. Mills
*Attorney, Agent, or Firm*—Michael J. Striker

[57] ABSTRACT

N-methylcarbanilic-[3-(ethoxycarbonylamino)-phenyl]-ester. The compound is a specific cotton herbicide. It is highly active against common weeds without causing harm to the cotton plants at any state of their development.

3 Claims, No Drawings

N-METHYLCARBANILIC-[3-(ETHOXYCARBONYLAMINO)-PHENYL]-ESTER AS A COTTON HERBICIDE

The invention concerns the method of preparing and using N-methylcarbanilic-[3-(ethoxycarbonylamino)-phenyl]-ester as a cotton herbicide.

The control of weeds in cotton cultures is rather problematic. Since the cotton plant is a dicotyledenous plant, it is particularly sensitive to weed control when it is directly affected by such weed control.

It was therefore necessary to develop a special weedicide which is preferably prepared substantially as follows:

1. Good seed preparation, so that the cotton can grow rapidly and uniformly. Higher seed rows are formed with mechanical means so that troughs are formed between the seed rows in which the weed can be controlled later by contact means.
2. Either before or after the formation of the seed rows, a known herbicide is incorporated for weed control.
3. During the seeding of the cotton it is treated with known herbicides, such as N-(3-trifluormethylphenyl)-N',N'-dimethyl urea (British Pat. No. 914,779) or N-(3,4-dichlorophenyl)-N'-N'-dimethyl urea (British Pat. No. 691-403) and as a rule by hand spraying for the additional control of possible sprouting grasses and dicotyledenous weeds.
4. Mechanical tilling of the soil is combined with underleaf spraying. As soon as the cotton has grown at least 15 cm high, these sprayings can be started. Preparations like monosodium methane arsonate (U.S. Pat. No. 2,442,372) or combinations of monosodium methane arsonate with N-(3-trifluormethylphenyl)-N',N'-dimethyl urea, 2,4-bis-(isopropylamino)-6-methylthio-S-triazine (British Pat. No. 814,948), N-(3,4-dichlorophenyl)-N',N'-dimethyl urea or N-(3,4-dichlorophenyl)-N'-methoxy-N'-methyl urea (British Pat. No. 852,422) are used in one to three sprayings.
5. Simultaneously with the mechanical tilling, the weed seedlings in the center and at the edges of the rows of cultivated plants are covered with the piled-up soil.

This control method is therefore not only extremely elaborate, it is also unsatisfactory for the solution of the weed problem in cotton, since weed plants must still be removed by being weeded and/or by weeding.

With the above in view it is an object of the present invention to provide a cotton herbicide which permits a technically simple control of weeds in cotton in any development stage of the cotton plant, while avoiding the disadvantages of the known herbicides.

This problem is solved according to the invention by a preparation which is characterized in that it contains N-methylcarbanilic-[3-(ethoxycarbonylamino)-phenyl]-ester as an active substance.

In accordance with the present invention the state of weed control is considerably simplified and thus facilitated and made cheaper. The preparation according to the invention can be applied in any development stage of the cotton plant, by spraying directly over the plant so as to also spray the weeds in the immediate proximity of the cotton plant.

The present invention permits an accurate application against existing weeds. It also controls sprouting weeds. The spraying can be repeated several times without any adverse effects on the cotton plant or following cultures. The spraying is to a great extent independent of the type of soil and of the weather after the spraying. All mechanical cultivating measures which serve to control weeds may be eliminated. It is to be noted that the compound according to the invention has a wide action spectrum.

The compound according to the invention can be used either per se or in combination with other active substances. If necessary, other defoliating agents, planticides or pesticides can be added, depending on the desired purpose.

The action and the rate of action can also be increased, for example, by action-enhancing additions, like organic solvents, wetting agents and oils. This permits the reduction in the amount of active substance proper to be used.

The above indicated active substance or its mixtures in the form of preparations, like powders, dusting powders, emulsions or suspensions, can be used with the addition of liquid and/or solid carrier substances or diluants and wetting, adhesive, emulsifying and/or dispersing agents, if necessary.

As liquid carrier substances there may be used water, aliphatic and aromatic hydrocarbons, such as benzene, toluene, xylene, cyclohexanone, isophorone, dimethylsulfoxide, dimethyl formamide, also mineral oil fractions.

As solid carrier substances there may be used mineral earths, such as clay sil, silica gel, kaolin, talcum, atta clay, limestone, silica acid and vegetable products, like flours.

Surface active substances that can be used are, for example, calcium lignin-sulfonate, polyoxyethylene-alkyl phenolether, naphthalene sulfonic acid and their salts, phenolsulfonic acids and their salts, formaldehyde condensates, fatty alcohol sulfates, as well as substituted benzene sulfonic acids and their salts.

The portion of the active substance used in the various preparations can vary within wide limits. For example, the preparations can contain about 10 to 80% by weight of active substances, about 90 to 20% by weight of liquid or solid carrier substances, as well as 20% surface-active substances, if necessary.

The preparations can be applied in the usual well-known manner, such as with water as a vehicle in spray solutions in amounts of about 100 to 1000 liter/ha. The preparations can be applied both in the "low-volume" and in the "ultra low-volume" method and also in the form of so-called microgranules.

The compound to be used according to the invention can be prepared, for example, by reacting (a) 3-hydroxycarbanilic ethyl ester with N-methylaniline and phosgene in an organic solvent
(b) 3-hydroxycarbanilic ethyl ester-alkali salt, particularly sodium salt, with N-methyl-N-phenyl carbamoyl halide in an organic solvent, or
(c) chloroformic acid-3-ethoxycarbonylamino-phenyl ester with N-methylaniline in a solvent in the presence of an acid acceptor, and isolating the reaction product in known manner.

The following examples will clearly illustrate the preparation of the compound according to the invention.

Preparation of N-methylcarbanilic[3-(ethoxycarbonylamino)phenyl]-ester

A. Into a solution of 9.89 g (0.1 mole) phosgene in 50 ml dioxane is added in drops at 20° to 25° C. a solution of 18.1 g (0.1 mole) 3-hydroxycarbanilic ethyl ester and 24.2 g (0.2 mole) N-methylaniline in 50 ml dioxane. Then the mixture is boiled for 90 minutes on the reflux and poured after cooling into ice water, the carbamate is extracted with ether, and the ether solution is washed with dilute soda lye and ice water and dried with magnesium sulfate. After evaporation of the ether, the carbamate crystallizes upon the addition of light gasoline.

Yield: 26.7 g,–85% of the theory.

B. 18.1 g 3-hydroxycarbanilic ethyl ester are dissolved in a solution of 0.1 mole sodium ethylate in 50 ml absolute ethanol. The solution is evaporated in the vacuum and the dry sodium salt is absorbed in 100 ml methyl isobutyl ketone. At 70° C., a solution of b 16.9 g N-methyl-N-phenylcarbamoyl-chloride in 40 ml methyl-isobutyl ketone is added in drops under stirring. The stirring is continued for 45 minutes at 70° C. After cooling, the product is washed at 0° C. with water and dilute soda lye, dried with magnesium sulfate, and evaporated under reduced pressure. The residue is crystallized from ether/pentane.

Yield: 20 g N-methylcarbanilic-[3-(ethoxycarbonylamino)phenyl]-ester=64% of the theory; Fp.=103°–104° C.

C. A solution of 330 g N-methylaniline in 1 liter acetic ester is mixed with 1 liter water. Subsequently a solution of 750 g chloroformic-3-ethoxycarbonylaminophenyl ester in 1.5 liter acetic ester, and at the same time a solution of 426 g potassium carbamate in 1.5 liter water are added in drops in 25 minutes under stirring and cooling to about 10°–14° C.

The stirring is continued for 30 minutes at 10° C. Then the organic phase is separated and washed at 0° C. with dilute soda lye, dilute hydrochloric acid and water, dried with magnesium sulfate, and evaporated under reduced pressure. The oily residue crystallizes from ether pentane.

Yield: 770 g N-methylcarbanilic-[3-(ethoxycarbonylamino)phenyl]-ester=79.5% of the theory.

Fp.=103°–104° C.

D. The production can also be effected by hydrating the N-methylcarbanilic-2-nitrophenyl ester e.g. in the presence of Raney nickel and subsequent reaction of the N-methylcarbanilic-3-aminophenyl ester with chloroformic ethyl ester.

N-methylcarbanilic-[3-(ethoxycarbonylamino)phenyl]-ester is soluble in ether, acetone, cyclohexanone, isophorone and dimethyl formamide.

It is insoluble in water and gasoline.

Furthermore, it will be noted that the following example will illustrate the herbicidal action of the compound to be used according to the invention.

EXAMPLE

The following plants were treated in the post-emergence method with N-methylcarbanilic-[3-(ethoxycarbonylamino)-phenyl]ester in an amount of 1 and 3 kg active substance/ha, emulsified in 500 liter water per ha.

As reference compounds there were used in the amounts listed below:

N-(3-trifluormethylphenyl)-N',N'-dimethyl urea
2,4-bis-(isopropylamino)-6-methylthio-S-triazine
N-(3,4-dichlorophenyl)-N',N'-dimethyl urea
N-(3,4-dichlorophenyl)-N'-methoxy-N'-methyl urea and
monosodium methane arsenate.

The success of the treatment was determined by appraisal. (0—total destruction, 10—no damage)

The values in the following table indicate the good culture tolerability of the compound according to the invention, while the known reference preparations showed considerable damages of the cultivated plants by spraying. Beyond that, the compound according to the invention is characterized by excellent action against weeds. In contrast, the herbicidal action of the reference compound is not satisfactory in many important weed species.

| COMPOUND ACCORDING TO THE INVENTION | kg/ha AS | cotton | datura sp. | ipomea sp. | sida sp. | abutilon sp. | xantium sp. | eleusine indrea | amaranthus sp. | setaria i. | echinochloa c.g |
|---|---|---|---|---|---|---|---|---|---|---|---|
| N-methylcarbanilic-[3-(ethoxyoarbonylamino)-phenyl]-ester | 1 | 10 | 0 | 0 | 0 | 0 | 0 | 0 | 0 | 0 | 0 |
|  | 3 | 10 | 0 | 0 | 0 | 0 | 0 | 0 | 0 | 0 | 0 |
| Reference Compounds |  |  |  |  |  |  |  |  |  |  |  |
| N-(3-trifluoromethylphenyl)-N',N'-dimethyl urea | 1 | 4 | 2 | 1 | 2 | 3 | 2 | 6 | 0 | 1 | 2 |
| 2,4-bis-(isopropylamino)-6-methylthio-S-triazine | 1 | 2 | 2 | 0 | 4 | 2 | 3 | 3 | 0 | 0 | 1 |
| N-(3,4-dichlorophenyl)-N',N'-dimethyl urea | 0.5 | 2 | 2 | 2 | 3 | 3 | 2 | 7 | 0 | 0 | 3 |
| N-(3,4-dichlorophenyl)-N'-methoxy-N'-methyl urea | 1 | 2 | 2 | 2 | 2 | 3 | 3 | 4 | 0 | 0 | 1 |
| Monodsodium methane arsonate | 1 | 2 | 6 | 5 | 4 | 5 | 4 | 3 | 0 | 1 | 3 |
| Untreated |  | 10 | 10 | 10 | 10 | 10 | 10 | 10 | 10 | 10 | 10 |

O = total destruction
10 = no damage

What is claimed herein is:

1. N-methylcarbanilic-[3-(ethoxycarbonylamino)-phenyl]ester having cotton-herbicidal action.

2. A composition for the control of weed growth in cotton fields consisting essentially of the compound of claim 1 as the active ingredient in an amount sufficient to substantially prevent the growth of weeds without causing substantial damage to the cotton plants together with an inert carrier.

3. The composition of claim 2 wherein said active ingredient is present in an amount between about 10 and about 80 percent by weight of said composition.